United States Patent [19]
Bonini et al.

[11] Patent Number: 6,117,990
[45] Date of Patent: Sep. 12, 2000

[54] DNA ENCODING SNORF1 RECEPTOR

[75] Inventors: James A. Bonini, Oakland; Beth E. Borowsky, Montclair, both of N.J.

[73] Assignee: Synaptic Pharmaceutical Corporation, Paramus, N.J.

[21] Appl. No.: 09/286,805

[22] Filed: Apr. 6, 1999

[51] Int. Cl.$^7$ .......................... C12N 15/12; C07K 14/705
[52] U.S. Cl. ......................... 536/23.5; 536/23.1; 536/24.3
[58] Field of Search .................................. 536/23.1, 23.5, 536/24.3; 530/350

[56] References Cited

U.S. PATENT DOCUMENTS 5,851,798  12/1998  Shabon et al. .......................... 435/69.1

*Primary Examiner*—Prema Mertz
*Assistant Examiner*—Fozia Hamud
*Attorney, Agent, or Firm*—John P. White; Cooper & Dunham LLP

[57] ABSTRACT

This invention provides a recombinant nucleic acid comprising a nucleic acid encoding a mammalian SNORF1 receptor, wherein the mammalian receptor-encoding nucleic acid hybridizes under high stringency conditions to (a) a nucleic acid encoding a human SNORF1 receptor and having a sequence identical to the sequence of the human SNORF1 receptor-encoding nucleic acid contained in plasmid pEXJ-hSNORF1-f (ATCC Accession No. 203898) or (b) a nucleic acid encoding a rat SNORF1 receptor and having a sequence identical to the sequence of the rat SNORF1 receptor-encoding nucleic acid contained in plasmid pcDNA3.1-rSNORF1-f (ATCC Accession No. 203897). This invention further provides a recombinant nucleic acid comprising a nucleic acid encoding a human SNORF1 receptor, wherein the human SNORF1 receptor comprises an amino acid sequence identical to the sequence of the human SNORF1 receptor encoded by the shortest open reading frame indicated in FIGS. 1A–1B (Seq. I.D. No. 1). This invention also provides a recombinant nucleic acid comprising a nucleic acid encoding a rat SNORF1 receptor, wherein the rat SNORF1 receptor comprises an amino acid sequence identical to the sequence of the rat SNORF1 receptor encoded by the shortest open reading frame indicated in FIGS. 3A–3B (Seq. I.D. No. 3).

4 Claims, 8 Drawing Sheets

FIGURE 1A

```
  1  CTCCTAGAAGACTTTGAAATTGCTTCCTTTAAAAAATTTTTGAAAGCAGGAATTTGAG    60
 61  AACTTTAAAATAGTTCAAACAAGAAAGCAATGGTGAATAATTCTCCCAAGCTGAGGCTG   120
121  TGGAGCTGTGTTACAAGAACGTGAACGAATCCCTGCATTAAAACTCCTTACTCGCCAGTC  180
181  CTCGATCTATCCTCTACGCCGTCCTTGGTTTTGGGGCTGTGCTGGCAGCCGTTTGGAAACT 240
241  TACTGGTCATGATTGCTATCCTTCACTTCAAACAACTGCACACACCTACAAACTTTCTGA  300
301  TTGCCGTCGCTGGCCTGTGCTGACTTCTTGGTGGGAGTCACTGTGATGCCCTTCAGCACAG 360
361  TGAGGTCTGTGGAGAGCTGTTGGTACTTTGGGGACAGTTACTGTAAATTCCATACATGTT  420
421  TTGACACATCCTCTGTTTTGCTTCTTTATTCATTTATGCTGTATCTCTGTTGATAGAT    480
481  ACATTGCTGTTACTGATCCTCTGACCTCCAACCAAGTTACTGTGTCAGTTTCAGGA      540
541  TATGCATTGTTCTTTCCTGGTTCTTTTCTGTCACATACAGCTTTTCGATCTTTTACACGG  600
601  GAGCCAACGAAGAAGGAATTGAGGAATTAGTAGTTGCTCTAACCTGTGTAGGAGGCTGCC  660
661  AGGCTCCACTGAATCAAAACTGGGTCCTACTTTGTTTTCTTCTTATTCTTTATACCCAATG 720
```

FIGURE 1B

```
721   TCGCCATGGTGTGTTTATATACAGTAAGATATTTTGGTGGCCAAGCATCAGGCTAGGAAGA   780
781   TAGAAAGTACAGCCAGCCAAGCTCAGTCCTCCTCAGAGAGTTACAAGGAAAGAGTAGCAA    840
841   AAAGAGAGAGAAAGGCTGCCAAAACCTTGGGAATTGCTATGGCAGCATTTCTTGTCTCTT   900
901   GGCTACCATACCTCGTTGATGCAGTGATTGATGCTTATATGAATTTTATAACTCCTCCTT   960
961   ATGTTTATGAGATTTTAGTTTGGTGTGTTTATTATAATTCAGCTATGAACCCCTTGATTT   1020
1021  ATGCTTTCTTTTACCAATGGTTTGGGAAGGCAATAAAACTTATTGTAAGCGGCAAGGTCT   1080
1081  TAAGGACTGATTCGTCAACAACTAATTTATTTCTGAAGAAGTAGAGACAGATTAAAAAC   1140
1141  ATTACTGTAGAGACCTCAAAACTAACTTGAAATTAAGGTCAAGTGCAAAAATAAACACTT   1200
1201  G                                                              1201
```

```
  1  CGGAAGACTCCATGGAGCTCTGCTACGAGAACGTGAATGGATCTTGCATTAAAAGCTCCT   60
 61  ACTCGCCCTGGCCTCGAGCCATCCTCTATGCGGTCCTTGGTTTGGGAGCCCTGCTGGCAG  120
121  TGTTTGGGAACTTACTGGTCATCACCGCTATCCTCCACTTAAACAGTTGCACACGCCTA   180
181  CAAACTTTCTGGTGGCCCTGGCCTGTGCTGGGTCTGCTGGAGGGCTGTGGGGTGACTGTGATGC  240
241  CCTTTAGCACGGTGCCGTTGCCGTGTACTTTGGGACACTTACTGTAAGT  300
301  TCCACACGTGTTCGACACCCACTGACCCTATCCGACCAAGTTCACCATCT  360
361  CCATTGACAGGTACGTTGCAGTCACCGACCTATCCGACCAAGTTCACCATTT  420
421  CGGTTTCGGCGTGTGCATCGCTCTCGTGGTTCTTTTCTGTCACCTACAGCTTTTCCA  480
481  TCTTTTACACAGGAGCTGCCAGGTCCCACTGAATCAGAATTGGGTTTTACTTTGTTCT  540
541  TGGGAGGCTGCCAGGCTCCACTGTCGTCATGGTGTTTCTCTATGGTCGGATATTTTGGTGGCAAGCAAC  600
601  TTCTGCCCACTGTCGTCATGGTGTTTCTCTATGGTCGGATATTTTTGGTGGCAAGCAAC  660
661  AGGCTAGGAAGATAGAGGGTTCGGCCAACCCCAGGCCTCCCTCTGAGAGCTACAAGG  720
```

FIGURE 3B

721  AAAGAGTAGCCAGACGAGAGAGGAAGGGGCCAAAACCTTGGGATCGCCATGGCTGCAT  780
781  TTCTCGTGTCCCTGGCTGCCTGCCATACATTATCGATGCCGTGATTGATGCCTACATGAACTTCA  840
841  TAACTCCCTGCCTACGTCTATGAGATATTAGTGTGGTGTGTTTACTATAATTCAGCTATGA  900
901  ACCCTTTGATATATGCCTTCTTTTATCCTTGGTTTCGCAAGGCAATAAAACTTATTGTGA  960
961  GTGGCAAAGTCTTCAGGGCTGACTCATCAAGAACTAATCTGTTCTCTGAAGAAGCAGGTG  1020
1021 CAGGTTAAGACAATCACGGCGGAGAGTTGACATCCGGCTAG  1061

DNA ENCODING SNORF1 RECEPTOR

BACKGROUND OF THE INVENTION

Throughout this application various publications are referred to by partial citations within parenthesis. Full citations for these publications may be found at the end of the specification immediately preceding the claims. The disclosures of these publications, in their entireties, are hereby incorporated by reference into this application in order to more fully describe the state of the art to which the invention pertains.

Neuroregulators comprise a diverse group of natural products that subserve or modulate communication in the nervous system. They include, but are not limited to, neuropeptides, amino acids, biogenic amines, lipids and lipid metabolites, and other metabolic byproducts. Many of these neuroregulator substances interact with specific cell surface receptors which transduce signals from the outside to the inside of the cell. G-protein coupled receptors (GPCRs) represent a major class of cell surface receptors with which many neurotransmitters interact to mediate their effects. GPCRs are characterized by seven membrane-spanning domains and are coupled to their effectors via G-proteins linking receptor activation with intracellular biochemical sequelae such as stimulation of adenylyl cyclase. While the structural motifs that characterize a GPCR can be recognized in the predicted amino acid sequence of a novel receptor, the endogenous ligand that activates the GPCR cannot necessarily be predicted from its primary structure. Thus, a novel receptor sequence may be designated as an orphan GPCR when it possesses the structural motif characteristic of a G-protein coupled receptor, but its endogenous ligand has not yet been defined.

SUMMARY OF THE INVENTION

This invention provides a recombinant nucleic acid comprising a nucleic acid encoding a mammalian SNORF1 receptor, wherein the mammalian receptor-encoding nucleic acid hybridizes under high stringency conditions to (a) a nucleic acid encoding a human SNORF1 receptor and having a sequence identical to the sequence of the human SNORF1 receptor-encoding nucleic acid contained in plasmid pEXJ-hSNORF1-f (ATCC Accession No. 203898) or (b) a nucleic acid encoding a rat SNORF1 receptor and having a sequence identical to the sequence of the rat SNORF1 receptor-encoding nucleic acid contained in plasmid pcDNA3.1-rSNORF1-f (ATCC Accession No. 203897).

This invention further provides a recombinant nucleic acid comprising a nucleic acid encoding a human SNORF1 receptor, wherein the human SNORF1 receptor comprises an amino acid sequence identical to the sequence of the human SNORF1 receptor encoded by the shortest open reading frame indicated in FIGS. 1A–1B (Seq. I.D. No. 1).

This invention also provides a recombinant nucleic acid comprising a nucleic acid encoding a rat SNORF1 receptor, wherein the rat SNORF1 receptor comprises an amino acid sequence identical to the sequence of the rat SNORF1 receptor encoded by the shortest open reading frame indicated in FIGS. 3A–3B (Seq. I.D. No. 3).

BRIEF DESCRIPTION OF THE FIGURES

FIGS. 1A–1B

Nucleotide sequence including sequence encoding a human SNORF1 receptor (Seq. I.D. No. 1). Putative open reading frames including the shortest open reading frame are indicated by underlining one start (ATG) codon (at positions 90–92) and the stop codon (at positions 1134–1136). In addition, partial 5' and 3' untranslated sequences are shown.

FIGS. 2A–2B

Deduced amino acid sequence (Seq. I.D. No. 2) of the human SNORF1 receptor encoded by the longest open reading frame indicated in the nucleotide sequence shown in FIGS. 1A–1B (Seq. I.D. No. 1). The seven putative transmembrane (TM) regions are underlined.

FIGS. 3A–3B

Nucleotide sequence including sequence encoding a rat SNORF1 receptor (Seq. I.D. No. 3). Putative open reading frames including the shortest open reading frame are indicated by underlining one start (ATG) codon (at positions 12–14) and the stop codon (at positions 1026–1028). In addition, partial 5' and 3' untranslated sequences are shown.

FIGS. 4A–4B

Deduced amino acid sequence (Seq. I.D. No. 4) of the rat SNORF1 receptor encoded by the longest open reading frame indicated in the nucleotide sequence shown in FIGS. 3A–3B (Seq. I.D. No. 3). The seven putative transmembrane (TM) regions are underlined.

DETAILED DESCRIPTION OF THE INVENTION

This invention provides a recombinant nucleic acid comprising a nucleic acid encoding a mammalian SNORF1 receptor, wherein the mammalian receptor-encoding nucleic acid hybridizes under high stringency conditions to (a) a nucleic acid encoding a human SNORF1 receptor and having a sequence identical to the sequence of the human SNORF1 receptor-encoding nucleic acid contained in plasmid pEXJ-hSNORF1-f (ATCC Accession No. 203898) or (b) a nucleic acid encoding a rat SNORF1 receptor and having a sequence identical to the sequence of the rat SNORF1 receptor-encoding nucleic acid contained in plasmid pcDNA3.1-rSNORF1-f (ATCC Accession No. 203897).

This invention further provides a recombinant nucleic acid comprising a nucleic acid encoding a human SNORF1 receptor, wherein the human SNORF1 receptor comprises an amino acid sequence identical to the sequence of the human SNORF1 receptor encoded by the shortest open reading frame indicated in FIGS. 1A–1B (Seq. I.D. No. 1).

This invention also provides a recombinant nucleic acid comprising a nucleic acid encoding a rat SNORF1 receptor, wherein the rat SNORF1 receptor comprises an amino acid sequence identical to the sequence of the rat SNORF1 receptor encoded by the shortest open reading frame indicated in FIGS. 3A–3B (Seq. I.D. No. 3).

The plasmid pEXJ-hSNORF1-f and plasmid pcDNA3.1-rSNORF1-f were both deposited on Apr. 5, 1999, with the American Type Culture Collection (ATCC), 10801 University Blvd., Manassas, Va. 20110-2209, U.S.A. under the provisions of the Budapest Treaty for the International Recognition of the Deposit of Microorganisms for the Purposes of Patent Procedure and were accorded ATCC Accession Nos. 203897 and 203898 respectively.

Hybridization methods are well known to those of skill in the art. For purposes of this invention, hybridization under high stringency conditions means hybridization performed at 40° C. in a hybridization buffer containing 50% formamide, 5× SSC, 7 mM Tris, 1× Denhardt's, 25 µg/ml salmon sperm DNA; wash at 50° C. in 0.1× SSC, 0.1% SDS.

The nucleic acids of this invention may be used as probes to obtain homologous nucleic acids from other species and to detect the existence of nucleic acids having complementary sequences in samples.

The nucleic acids may also be used to express the receptors they encode in transfected cells.

Also, use of the receptor encoded by the SNORF1 receptor nucleic acid sequence enables the discovery of the endogenous ligand.

The use of a constitutively active receptor encoded by SNORF1 either occurring naturally without further modification or after appropriate point mutations, deletions or the like, allows screening for antagonists and in vivo use of such antagonists to attribute a role to receptor SNORF1 without prior knowledge of the endogenous ligand.

Use of the nucleic acids further enables elucidation of possible receptor diversity and of the existence of multiple subtypes within a family of receptors of which SNORF1 is a member.

Finally, it is contemplated that this receptor will serve as a valuable tool for designing drugs for treating various pathophysiological conditions such as chronic and acute inflammation, arthritis, autoimmune diseases, transplant rejection, graft vs. host disease, bacterial, fungal, protozoan and viral infections, septicemia, AIDS, pain, psychotic and neurological disorders, including anxiety, depression, schizophrenia, dementia, mental retardation, memory loss, epilepsy, locomotor problems, respiratory disorders, asthma, eating/body weight disorders including obesity, bulimia, diabetes, anorexia, nausea, hypertension, hypotension, vascular and cardiovascular disorders, ischemia, stroke, cancers, ulcers, urinary retention, sexual/reproductive disorders, circadian rhythm disorders, renal disorders, bone diseases including osteoporosis, benign prostatic hypertrophy, gastrointestinal disorders, nasal congestion, allergies, Parkinson's disease, Alzheimer's disease, among others and diagnostic assays for such conditions.

Methods of transfecting cells e.g. mammalian cells, with such nucleic acid to obtain cells in which the receptor is expressed on the surface of the cell are well known in the art. (See, for example, U.S. Pat. Nos. 5,053,337; 5,155,218; 5,360,735; 5,472,866; 5,476,782; 5,516,653; 5,545,549; 5,556,753; 5,595,880; 5,602,024; 5,639,652; 5,652,113; 5,661,024; 5,766,879; 5,786,155; and 5,786,157, the disclosures of which are hereby incorporated by reference in their entireties into this application.)

Such transfected cells may also be used to test compounds and screen compound libraries to obtain compounds which bind to the orphan SNORF1 receptor, as well as compounds which activate or inhibit activation of functional responses in such cells, and therefore are likely to do so in vivo. (See, for example, U.S. Pat. Nos. 5,053,337; 5,155,218; 5,360, 735; 5,472,866; 5,476,782; 5,516,653; 5,545,549; 5,556, 753; 5,595,880; 5,602,024; 5,639,652; 5,652,113; 5,661, 024; 5,766,879; 5,786,155; and 5,786,157, the disclosures of which are hereby incorporated by reference in their entireties into this application.)

Host cells

A broad variety of host cells can be used to study heterologously expressed proteins. These cells include but are not limited to mammalian cell lines such as; Cos-7, CHO, LM(tk−), HEK293, etc.; insect cell lines such as; Sf9, Sf21, etc.; amphibian cells such as *xenopus oocytes;* assorted yeast strains; assorted bacterial cell strains; and others. Culture conditions for each of these cell types is specific and is known to those familiar with the art.

Transient expression

DNA encoding proteins to be studied can be transiently expressed in a variety of mammalian, insect, amphibian, yeast, bacterial and other cells lines by several transfection methods including but not limited to; calcium phosphate-mediated, DEAE-dextran mediated; liposomal-mediated, viral-mediated, electroporation-mediated, and microinjection delivery. Each of these methods may require optimization of assorted experimental parameters depending on the DNA, cell line, and the type of assay to be subsequently employed.

Stable expression

Heterologous DNA can be stably incorporated into host cells, causing the cell to perpetually express a foreign protein. Methods for the delivery of the DNA into the cell are similar to those described above for transient expression but require the co-transfection of an ancillary gene to confer drug resistance on the targeted host cell. The ensuing drug resistance can be exploited to select and maintain cells that have taken up the DNA. An assortment of resistance genes are available including but not restricted to neomycin, kanamycin, and hygromycin. For the purposes of studies concerning the orphan receptor of this invention, stable expression of a heterologous receptor protein is typically carried out in, mammalian cells including but not necessarily restricted to, CHO, HEK293, LM(tk−), etc.

In addition native cell lines that naturally carry and express the nucleic acid sequences for the given orphan receptor may be used without the need to engineer the receptor complement.

Membrane preparations

Cell membranes expressing the orphan receptor protein of this invention are useful for certain types of assays including but not restricted to ligand binding assays, GTP-γ-S binding assays, and others. The specifics of preparing such cell membranes may in some cases be determined by the nature of the ensuing assay but typically involve harvesting whole cells and disrupting the cell pellet by sonication in ice cold buffer (e.g. 20 mM Tris-HCl, 5 mM EDTA, pH 7.4). The resulting crude cell lysate is cleared of cell debris by low speed centrifugation at 200× g for 5 min at 4° C. The cleared supernatant is then centrifuged at 40,000× g for 20 min at 4° C., and the resulting membrane pellet is washed by suspending in ice cold buffer and repeating the high speed centrifugation step. The final washed membrane pellet is resuspended in assay buffer. Protein concentrations are determined by the method of Bradford (1976) using bovine serum albumin as a standard. The membranes may be used immediately or frozen for later use.

Generation of baculovirus

The coding region of DNA encoding the human receptor disclosed herein may be subcloned into pBlueBacIII into existing restriction sites or sites engineered into sequences 5' and 3' to the coding region of the polypeptides. To generate baculovirus, 0.5 μg of viral DNA (BaculoGold) and 3 μg of DNA construct encoding a polypeptide may be co-transfected into 2×10⁶ *Spodoptera frugiperda* insect Sf9 cells by the calcium phosphate co-precipitation method, as outlined by Pharmingen (in "Baculovirus Expression Vector System: Procedures and Methods Manual"). The cells then are incubated for 5 days at 27° C.

The supernatant of the co-transfection plate may be collected by centrifugation and the recombinant virus plaque purified. The procedure to infect cells with virus, to prepare stocks of virus and to titer the virus stocks are as described in Pharmingen's manual.

Labeled ligand binding assays

Cells expressing the orphan receptor of this invention may be used to screen for ligands for said receptors, for example, by labeled ligand binding assays. Once a ligand is identified the same assays may be used to identify agonists or antagonists of the orphan receptor that may be employed for a variety of therapeutic purposes.

In an embodiment, labeled ligands are placed in contact with either membrane preparations or intact cells expressing the orphan receptor in multi-well microtiter plates, together with unlabeled compounds, and binding buffer. Binding reaction mixtures are incubated for times and temperatures determined to be optimal in separate equilibrium binding assays. The reaction is stopped by filtration through GF/B filters, using a cell harvester, or by directly measuring the bound ligand. If the ligand was labeled with a radioactive isotope such as H, $^{14}C$, $^{125}I$, $^{35}S$ $^{32}P$, $^{33}P$, etc., the bound ligand may be detected by using liquid scintillation counting, scintillation proximity, or any other method of detection for radioactive isotopes. If the ligand was labeled with a fluorescent compound, the bound labeled ligand may be measured by methods such as, but not restricted to, fluorescence intensity, time resolved fluorescence, fluorescence polarization, fluorescence transfer, or fluorescence correlation spectroscopy. In this manner agonist or antagonist compounds that bind to the orphan receptor may be identified as they inhibit the binding of the labeled ligand to the membrane protein or intact cells expressing the said receptor. Non-specific binding is defined as the amount of labeled ligand remaining after incubation of membrane protein in the presence of a high concentration (e.g., $100-1000 \times K_D$) of unlabeled ligand. In equilibrium saturation binding assays membrane preparations or intact cells transfected with the orphan receptor are incubated in the presence of increasing concentrations of the labeled compound to determine the binding affinity of the labeled ligand. The binding affinities of unlabeled compounds may be determined in equilibrium competition binding assays, using a fixed concentration of labeled compound in the presence of varying concentrations of the displacing ligands.

Functional assays

Cells expressing the orphan receptor DNA of this invention may be used to screen for ligands to said receptor using functional assays. Once a ligand is identified the same assays may be used to identify agonists or antagonists of the orphan receptor that may be employed for a variety of therapeutic purposes. It is well known to those in the art that the over-expression of a G-protein coupled receptor can result in the constitutive activation of intracellular signaling pathways. In the same manner, over-expression of the orphan receptor in any cell line as described above, can result in the activation of the functional responses described below, and any of the assays herein described can be used to screen for both agonist and antagonist ligands of the orphan receptor.

A wide spectrum of assays can be employed to screen for the presence of orphan receptor ligands. These assays range from traditional measurements of total inositol phosphate accumulation, cAMP levels, intracellular calcium mobilization, and potassium currents, for example; to systems measuring these same second messengers but which have been modified or adapted to be of higher throughput, more generic and more sensitive; to cell based assays reporting more general cellular events resulting from receptor activation such as metabolic changes, differentiation, cell division/proliferation. Description of several such assays follow.

Cyclic AMP (cAMP) assay

The receptor-mediated stimulation or inhibition of cyclic AMP (cAMP) formation may be assayed in cells expressing the receptors. Cells are plated in 96-well plates or other vessels and preincubated in a buffer such as HEPES buffered saline (NaCl (150 mM), $CaCl_2$ (1 mM), KCl (5 mM), glucose (10 mM)) supplemented with a phosphodiesterase inhibitor such as 5mM theophylline, with or without protease inhibitor cocktail (For example, a typical inhibitor cocktail contains 2 $\mu g/ml$ aprotinin, 0.5 mg/ml leupeptin, and 10 $\mu g/ml$ phosphoramidon.) for 20 min at 37° C., in 5% $CO_2$. Test compounds are added with or without 10 mM forskolin and incubated for an additional 10 min at 37° C. The medium is then aspirated and the reaction stopped by the addition of 100 mM HCl or other methods. The plates are stored at 4° C. for 15 min, and the cAMP content in the stopping solution is measured by radioimmunoassay. Radioactivity may be quantified using a gamma counter equipped with data reduction software. Specific modifications may be performed to optimize the assay for the orphan receptor or to alter the detection method of cAMP.

Arachidonic acid release assay

Cells expressing the orphan receptor are seeded into 96 well plates or other vessels and grown for 3 days in medium with supplements. $^3H$-arachidonic acid (specific activity= 0.75 $\mu Ci/ml$) is delivered as a 100 $\mu L$ aliquot to each well and samples are incubated at 37° C., 5% $CO_2$ for 18 hours. The labeled cells are washed three times with medium. The wells are then filled with medium and the assay is initiated with the addition of test compounds or buffer in a total volume of 250 $\mu L$. Cells are incubated for 30 min at 37° C., 5% $CO_2$. Supernatants are transferred to a microtiter plate and evaporated to dryness at 75° C. in a vacuum oven. Samples are then dissolved and resuspended in 25 $\mu L$ distilled water. Scintillant (300 $\mu L$) is added to each well and samples are counted for $^3H$ in a Trilux plate reader. Data are analyzed using nonlinear regression and statistical techniques available in the GraphPAD Prism package (San Diego, Calif.).

Intracellular calcium mobilization assays

The intracellular free calcium concentration may be measured by microspectrofluorimetry using the fluorescent indicator dye Fura-2/AM (Bush et al, 1991). Cells expressing the receptor are seeded onto a 35 mm culture dish containing a glass coverslip insert and allowed to adhere overnight. Cells are then washed with HBS and loaded with 100 $\mu L$ of Fura-2/AM (10 $\mu M$) for 20 to 40 min. After washing with HBS to remove the Fura-2/AM solution, cells are equilibrated in HBS for 10 to 20 min. Cells are then visualized under the 40× objective of a Leitz Fluovert FS microscope and fluorescence emission is determined at 510 nM with excitation wavelengths alternating between 340 nM and 380 nM. Raw fluorescence data are converted to calcium concentrations using standard calcium concentration curves and software analysis techniques.

In another method, the measurement of intracellular calcium can also be performed on a 96-well (or higher) format and with alternative calcium-sensitive indicators, preferred examples of these are: aequorin, Fluo-3, Fluo-4, Fluo-5, Calcium Green-1, Oregon Green, and 488 BAPTA. After activation of the receptors with agonist ligands the emission elicited by the change of intracellular calcium concentration can be measured by a luminometer, or a fluorescence imager; a preferred example of this is the fluorescence imager plate reader (FLIPR).

Cells expressing the receptor of interest are plated into clear, flat-bottom, black-wall 96-well plates (Costar) at a density of 30,000–80,000 cells per well and allowed to incubate over night at 5% $CO_2$, 37° C. The growth medium is aspirated and 100 $\mu l$ of dye loading medium is added to each well. The loading medium contains: Hank's BSS (without phenol red)(Gibco), 20 mM HEPES (Sigma), 0.1%

BSA (Sigma), dye/pluronic acid mixture (e.g. 1 mM Flou-3, AM (Molecular Probes), 10% pluronic acid (Molecular Probes); (mixed immediately before use), and 2.5 mM probenecid (Sigma) (prepared fresh)). The cells are allowed to incubate for about 1 hour at 5% $CO_2$, 37° C.

During the dye loading incubation the compound plate is prepared. The compounds are diluted in wash buffer (Hank's BSS without phenol red), 20 mM HEPES, 2.5 mM probenecid to a 3× final concentration and aliquoted into a clear v-bottom plate (Nunc). Following the incubation the cells are washed to remove the excess dye. A Denley plate washer is used to gently wash the cells 4 times and leave a 100 μl final volume of wash buffer in each well. The cell plate is placed in the center tray and the compound plate is placed in the right tray of the FLIPR. The FLIPR software is setup for the experiment, the experiment is run and the data are collected. The data are then analyzed using an excel spreadsheet program.

Antagonist ligands are identified by the inhibition of the signal elicited by agonist ligands.

Inositol phosphate assay

Receptor mediated activation of the inositol phosphate (IP) second messenger pathways may be assessed by radiometric or other measurement of IP products.

For example, in a 96 well microplate format assay, cells are plated at a density of 70,000 cells per well and allowed to incubate for 24 hours. The cells are then labeled with 0.5 μCi [$^3$H]myo-inositol overnight at 37° C., 5% $CO_2$. Immediately before the assay, the medium is removed and replaced with 90 μL of PBS containing 10 mM LiCl. The plates are then incubated for 15 min at 37° C., 5% $CO_2$. Following the incubation, the cells are challenged with agonist (10 μl/well; 10× concentration) for 30 min at 37° C., 5% $CO_2$. The challenge is terminated by the addition of 100 μL of 50% v/v trichloroacetic acid, followed by incubation at 4° C. for greater than 30 minutes. Total IPs are isolated from the lysate by ion exchange chromatography. Briefly, the lysed contents of the wells are transferred to a Multi-screen HV filter plate (Millipore) containing Dowex AGI-X8 (200–400 mesh, formate form). The filter plates are prepared adding 100 μL of Dowex AG1-X8 suspension (50% v/v, water: resin) to each well. The filter plates are placed on a vacuum manifold to wash or elute the resin bed. Each well is first washed 2 times with 200 μl of 5 mM myo-inositol. Total [$^3$H] inositol phosphates are eluted with 75 μl of 1.2 M ammonium formate/0.1 M formic acid solution into 96-well plates. 200 μL of scintillation cocktail is added to each well, and the radioactivity is determined by liquid scintillation counting.

GTPγS functional assay

Membranes from cells expressing the orphan receptor are suspended in assay buffer (e.g., 50 mM Tris, 100 mM NaCl, 5 mM $MgCl_2$, 10 μM GDP, pH 7.4) with or without protease inhibitors (e.g., 0.1% bacitracin). Membranes are incubated on ice for 20 minutes, transferred to a 96-well Millipore microtiter GF/C filter plate and mixed with GTPγ$^{35}$S (e.g., 250,000 cpm/sample, specific activity ~1000 Ci/mmol) plus or minus unlabeled GTPγS (final concentration 100 μM). Final membrane protein concentration≈90 μg/ml. Samples are incubated in the presence or absence of test compounds for 30 min. at room temperature, then filtered on a Millipore vacuum manifold and washed three times with cold (4° C.) assay buffer. Samples collected in the filter plate are treated with scintillant and counted for $^{35}$S in a Trilux (Wallac) liquid scintillation counter. It is expected that optimal results are obtained when the receptor membrane preparation is derived from an appropriately engineered heterologous expression system, i.e., an expression system resulting in high levels of expression of the receptor and/or expressing G-proteins having high turnover rates (for the exchange of GDP for GTP). GTPYS assays are well-known to those skilled in the art, and it is contemplated that variations on the method described above, such as are described by Tian et al. (1994) or Lazareno and Birdsall (1993), may be used.

Microphysiometric assay

Because cellular metabolism is intricately involved in a broad range of cellular events (including receptor activation of multiple messenger pathways), the use of microphysiometric measurements of cell metabolism can in principle provide a generic assay of cellular activity arising from the activation of any orphan receptor regardless of the specifics of the receptor's signaling pathway.

General guidelines for transient receptor expression, cell preparation and microphysiometric recording are described elsewhere (Salon, J. A. and Owicki, J. A., 1996). Typically cells expressing receptors are harvested and seeded at $3\times10^5$ cells per microphysiometer capsule in complete media 24 hours prior to an experiment. The media is replaced with serum free media 16 hours prior to recording to minimize non-specific metabolic stimulation by assorted and ill-defined serum factors. On the day of the experiment the cell capsules are transferred to the microphysiometer and allowed to equilibrate in recording media (low buffer RPMI 1640, no bicarbonate, no serum (Molecular Devices Corporation, Sunnyvale, Calif.) containing 0.1% fatty acid free BSA), during which a baseline measurement of basal metabolic activity is established.

A standard recording protocol specifies a 100 μl/min flow rate, with a 2 min total pump cycle which includes a 30 sec flow interruption during which the acidification rate measurement is taken. Ligand challenges involve a 1 min 20 sec exposure to the sample just prior to the first post challenge rate measurement being taken, followed by two additional pump cycles for a total of 5 min 20 sec sample exposure. Typically, drugs in a primary screen are presented to the cells at 10 μM final concentration. Follow up experiments to examine dose-dependency of active compounds are then done by sequentially challenging the cells with a drug concentration range that exceeds the amount needed to generate responses ranging from threshold to maximal levels. Ligand samples are then washed out and the acidification rates reported are expressed as a percentage increase of the peak response over the baseline rate observed just prior to challenge.

MAP kinase assay

MAP kinase (mitogen activated kinase) may be monitored to evaluate receptor activation. MAP kinase is activated by multiple pathways in the cell. A primary mode of activation involves the ras/raf/MEK/MAP kinase pathway. Growth factor (tyrosine kinase) receptors feed into this pathway via SHC/Grb-2/SOS/ras. Gi coupled receptors are also known to activate ras and subsequently produce an activation of MAP kinase. Receptors that activate phospholipase C (such as Gq/G11-coupled) produce diacylglycerol (DAG) as a consequence of phosphatidyl inositol hydrolysis. DAG activates protein kinase C which in turn phosphorylates MAP kinase.

MAP kinase activation can be detected by several approaches. One approach is based on an evaluation of the phosphorylation state, either unphosphorylated (inactive) or phosphorylated (active). The phosphorylated protein has a slower mobility in SDS-PAGE and can therefore be compared with the unstimulated protein using Western blotting. Alternatively, antibodies specific for the phosphorylated protein are available (New England Biolabs) which can be used to detect an increase in the phosphorylated kinase. In either method, cells are stimulated with the test compound and then extracted with Laemmli buffer. The soluble fraction is applied to an SDS-PAGE gel and proteins are transferred electrophoretically to nitrocellulose or Immobilon. Immunoreactive bands are detected by standard Western blotting technique. Visible or chemiluminescent signals are recorded on film and may be quantified by densitometry.

Another approach is based on evaluation of the MAP kinase activity via a phosphorylation assay. Cells are stimulated with the test compound and a soluble extract is prepared. The extract is incubated at 30° C. for 10 min with gamma-$^{32}$P-ATP, an ATP regenerating system, and a specific substrate for MAP kinase such as phosphorylated heat and acid stable protein regulated by insulin, or PHAS-I. The reaction is terminated by the addition of $H_3PO_4$ and samples are transferred to ice. An aliquot is spotted onto Whatman P81 chromatography paper, which retains the phosphorylated protein. The chromatography paper is washed and counted for $^{32}$P in a liquid scintillation counter. Alternatively, the cell extract is incubated with gamma-$^{32}$P-ATP, an ATP regenerating system, and biotinylated myelin basic protein bound by streptavidin to a filter support. The myelin basic protein is a substrate for activated MAP kinase. The phosphorylation reaction is carried out for 10 min at 30° C. The extract can then by aspirated through the filter, which retains the phosphorylated myelin basic protein. The filter is washed and counted for $^{32}$P by liquid scintillation counting.

Cell Proliferation assay

Receptor activation of the orphan receptor may lead to a mitogenic or proliferative response which can be monitored via $^{3}$H-thymidine uptake. When cultured cells are incubated with $^{3}$H-thymidine, the thymidine translocates into the nuclei where it is phosphorylated to thymidine triphosphate. The nucleotide triphosphate is then incorporated into the cellular DNA at a rate that is proportional to the rate of cell growth. Typically, cells are grown in culture for 1–3 days. Cells are forced into quiescence by the removal of serum for 24 hrs. A mitogenic agent is then added to the media. 24 hrs later, the cells are incubated with $^{3}$H-thymidine at specific activities ranging from 1 to 10 $\mu$Ci/ml for 2–6 hrs. Harvesting procedures may involve trypsinization and trapping of cells by filtration over GF/C filters with or without a prior incubation in TCA to extract soluble thymidine. The filters are processed with scintillant and counted for $^{3}$H by liquid scintillation counting. Alternatively, adherent cells are fixed in MeOH or TCA, washed in water, and solubilized in 0.05% deoxycholate/0.1 N NaOH. The soluble extract is transferred to scintillation vials and counted for $^{3}$H by liquid scintillation counting.

Alternatively, cell proliferation can be assayed by measuring the expression of an endogenous or heterologous gene product, expressed by the cell line used to transfect the orphan receptor, which can be detected by methods such as, but not limited to, florescence intensity, enzymatic activity, immunoreactivity, DNA hybridization, polymerase chain reaction, etc.

Promiscuous second messenger assays

It is not possible to predict, a priori and based solely upon the GPCR sequence, which of the cell's many different signaling pathways any given orphan receptor will naturally use. It is possible, however, to coax receptors of different functional classes to signal through a pre-selected pathway through the use of promiscuous G, subunits. For example, by providing a cell based receptor assay system with an endogenously supplied promiscuous $G_\alpha$ subunit such as $G_{\alpha 15}$ or $G_{\alpha 16}$ or a chimeric $G_\alpha$ subunit such as $G_{\alpha q z}$, a GPCR, which might normally prefer to couple through a specific signaling pathway (e.g., $G_s$, $G_i$, $G_q$, $G_o$, etc.), can be made to couple through the pathway defined by the promiscuous $G_\alpha$ subunit and upon agonist activation produce the second messenger associated with that subunit's pathway. In the case of $G_{\alpha 15}$, $G_{\alpha 16}$ and/or $G_{\alpha q z}$ this would involve activation of the $G_q$ pathway and production of the second messenger $IP_3$. Through the use of similar strategies and tools, it is possible to bias receptor signaling through pathways producing other second messengers such as $Ca^{++}$, cAMP, and $K^+$ currents, for example (Milligan, 1999).

It follows that the promiscuous interaction of the exogenously supplied $G_\alpha$ subunit with the orphan receptor alleviates the need to carry out a different assay for each possible signaling pathway and increases the chances of detecting a functional signal upon receptor activation.

Methods for recording currents in Xenopus oocytes

Oocytes are harvested from Xenopus laevis and injected with mRNA transcripts as previously described (Quick and Lester, 1994; Smith et al., 1997). The test orphan receptor of this invention and G$\alpha$ subunit RNA transcripts are synthesized using the T7 polymerase ("Message Machine," Ambion) from linearized plasmids or PCR products containing the complete coding region of the genes. Oocytes are injected with 10 ng synthetic receptor RNA and incubated for 3–8 days at 17 degrees. Three to eight hours prior to recording, oocytes are injected with 500 pg promiscuous G$\alpha$ subunits mRNA in order to observe coupling to $Ca^{++}$ activated $Cl^-$ currents. Dual electrode voltage clamp (Axon Instruments Inc.) is performed using 3 M KCl-filled glass microelectrodes having resistances of 1–2 MOhm. Unless otherwise specified, oocytes are voltage clamped at a holding potential of −80 mV. During recordings, oocytes are bathed in continuously flowing (1–3 ml/min) medium containing 96 mM NaCl, 2 mM KCl, 1.8 mM $CaCl_2$, 1 mM $MgCl_2$, and 5 mM HEPES, pH 7.5 (ND96). Drugs are applied either by local perfusion from a 10 $\mu$l glass capillary tube fixed at a distance of 0.5 mm from the oocyte, or by switching from a series of gravity fed perfusion lines.

Other oocytes may be injected with a mixture of orphan receptor mRNAs and synthetic mRNA encoding the genes for G-protein-activated inward rectifier channels (GIRK1 and GIRK4, U.S. Pat. Nos. 5,734,021 and 5,728,535 or GIRK1 and GIRK2) or any other appropriate combinations (see, e.g., Inanobe et al., 1999). Genes encoding G-protein inwardly rectifying $K^+$ (GIRK) channels 1, 2 and 4 (GIRK1, GIRK2, and GIRK4) may be obtained by PCR using the published sequences (Kubo et al., 1993; Dascal et al., 1993; Krapivinsky et al., 1995 and 1995b) to derive appropriate 5' and 3' primers. Human heart or brain cDNA may be used as template together with appropriate primers.

Heterologous expression of GPCRs in Xenopus oocytes has been widely used to determine the identity of signaling pathways activated by agonist stimulation (Gundersen et al., 1983; Takahashi et al., 1987.). Activation of the phospholipase C (PLC) pathway is assayed by applying test compound in ND96 solution to oocytes previously injected with mRNA for the mammalian orphan receptor (with or without promiscuous G proteins) and observing inward currents at a holding potential of −80 mV. The appearance of currents that reverse at −25 mV and display other properties of the $Ca^{++}$-activated $Cl^-$ (chloride) channel is indicative of mammalian receptor-activation of PLC and release of IP3 and intracellular $Ca^{++}$. Such activity is exhibited by GPCRs that couple to $G_q$ or $G_{11}$.

Measurement of inwardly rectifying $K^+$ (potassium) channel (GIRK) activity may be monitored in oocytes that have been co-injected with mRNAs encoding the mammalian orphan receptor plus GIRK subunits. GIRK gene products co-assemble to form a G-protein activated potassium channel known to be activated (i.e., stimulated) by a number of GPCRs that couple to $G_i$ or $G_o$ (Kubo et al., 1993; Dascal et al., 1993). Oocytes expressing the mammalian orphan receptor plus the GIRK subunits are tested for test compound responsivity by measuring $K^+$ currents in elevated $K^+$ solution containing 49 mM $K^+$.

This invention further provides an antibody capable of binding to a mammalian orphan receptor encoded by a nucleic acid encoding a mammalian orphan receptor. In one embodiment, the mammalian orphan receptor is a rat orphan receptor. In another embodiment, the mammalian orphan receptor is a human orphan receptor. This invention also provides an agent capable of competitively inhibiting the binding of the antibody to a mammalian orphan receptor. In one embodiment, the antibody is a monoclonal antibody or antisera.

This invention also provides a nucleic acid probe comprising at least 15 nucleotides, which probe specifically hybridizes with a nucleic acid encoding a mammalian orphan receptor, wherein the probe has a sequence corresponding to a unique sequence present within one of the two strands of the nucleic acid encoding the mammalian orphan receptor and are contained in plasmid pEXJ-hSNORF1-f (ATCC Accession No. 203898) or plasmid pcDNA3.1-rSNORF1-f (ATCC Accession No. 203897). This invention also provides a nucleic acid probe comprising at least 15 nucleotides, which probe specifically hybridizes with a nucleic acid encoding a mammalian orphan receptor, wherein the probe has a sequence corresponding to a unique sequence present within (a) the nucleic acid sequence shown in FIG. 1A–1B (Seq. I.D. No. 1) or (b) the reverse complement thereto. This invention also provides a nucleic acid probe comprising at least 15 nucleotides, which probe specifically hybridizes with a nucleic acid encoding a mammalian orphan receptor, wherein the probe has a sequence corresponding to a unique sequence present within (a) the nucleic acid sequence shown in FIG. 3A–3B (Seq. I.D. No. 3) or (b) the reverse complement thereto. In one embodiment, the nucleic acid is DNA. In another embodiment, the nucleic acid is RNA.

As used herein, the phrase "specifically hybridizing" means the ability of a nucleic acid molecule to recognize a nucleic acid sequence complementary to its own and to form double-helical segments through hydrogen bonding between complementary base pairs.

Methods of preparing and employing antisense oligonucleotides, antibodies, nucleic acid probes and transgenic animals directed to the orphan SNORF1 receptor are well known in the art. (See, for example, U.S. Pat. Nos. 5,053,337; 5,155,218; 5,360,735; 5,472,866; 5,476,782; 5,516,653; 5,545,549; 5,556,753; 5,595,880; 5,602,024; 5,639,652; 5,652,113; 5,661,024; 5,766,879; 5,786,155; and 5,786,157, the disclosures of which are hereby incorporated by reference in their entireties into this application.)

REFERENCES

Bradford, M. M., "A rapid and sensitive method for the quantitation of microgram quantities of protein utilizing the principle of protein-dye binding", Anal. Biochem. 72: 248–254 (1976).

Bush, et al., "Nerve growth factor potentiates bradykinin-induced calcium influx and release in PC12 cells" J. Neurochem. 57: 562–574(1991).

Dascal, N., et al., "Atrial G protein-activated $K^+$ channel: expression cloning and molecular properties" Proc. Natl. Acad. Sci. USA 90:10235–10239 (1993).

Gundersen, C. B., et al., "Serotonin receptors induced by exogenous messenger RNA in Xenopus oocytes" Proc. R. Soc. Lond. B. Biol. Sci. 219(1214): 103–109 (1983).

Inanobe, A., et al., "Characterization of G-protein-gated $K^+$ channels composed of Kir3.2 subunits in dopaminergic neurons of the substantia nigra" J. of Neuroscience 19(3):1006–1017 (1999).

Krapivinsky, G., et al., "The G-protein-gated atrial K+channel IKACh is a heteromultimer of two inwardly rectifying K($^+$)-channel proteins" Nature 374:135–141 (1995).

Krapivinsky, G., et al., "The cardiac inward rectifier $K^+$ channel subunit, CIR, does not comprise the ATP-sensitive $K^+$ channel, IKATP" J. Biol. Chem. 270:28777–28779 (1995b).

Kubo, Y., et al., "Primary structure and functional expression of a rat G-protein-coupled muscarinic potassium channel" Nature 364:802–806 (1993).

Lazareno, S. and Birdsall, N. J. M. "Pharmacological characterization of acetylcholine stimulated [35S]-GTPgS binding mediated by human muscarinic m1–m4 receptors: antagonist studies", Br. J. Pharmacology 109: 1120–1127 (1993)

Milligan, G., et al., "Use of chimeric Gα proteins in drug discovery" TIPS (In press).

Quick, M. W. and Lester, H. A., "Methods for expression of excitability proteins in Xenopus oocytes", Meth. Neurosci. 19: 261–279 (1994).

Salon, J. A. and Owicki, J. A., "Real-time measurements of receptor activity: Application of microphysiometic techniques to receptor biology" Methods in Neuroscience 25: pp. 201–224, Academic Press (1996).

Smith, K. E., et al., "Expression cloning of a rat hypothalamic galanin receptor coupled to phosphoinositide turnover." J. Biol. Chem. 272: 24612–24616 (1997).

Takahashi, T., et al., "Rat brain serotonin receptors in Xenopus oocytes are coupled by intracellular calcium to endogenous channels." Proc. Natl. Acad. Sci. USA 84(14): 5063–5067 (1987)

Tian, W., et al., "Determinants of alpha-Adrenergic Receptor Activation of G protein: Evidence for a Precoupled Receptor/G protein State." Molecular Pharmacology 45: 524–553 (1994).

What is claimed is:

1. A recombinant nucleic acid comprising a nucleic acid encoding a human SNORF1 receptor, wherein the human SNORF1 receptor comprises an amino acid sequence identical to the sequence of the human SNORF1 receptor encoded by the nucleotide sequences beginning at the start codon at positions 90–92 and ending at the stop codon at positions 1134–1336 as indicated in FIGS. 1A–1B (SEQ ID NO: 1).

2. A recombinant nucleic acid comprising a nucleic acid encoding a rat SNORF1 receptor, wherein the rat SNORF1 receptor comprises an amino acid sequence identical to the sequence of the rat SNORF1 receptor encoded by the nucleotide sequence beginning at the start codon at Positions 12–14 and ending at the stop codon at positions 1026–1028 as indicated in FIGS. 3A–3B (SEQ ID NO: 3).

3. A recombinant nucleic acid comprising a nucleic acid encoding a human SNORF1 receptor, wherein the nucleic acid has a sequence identical to the sequence of the human SNORF1 receptor-encoding nucleic acid contained in plasmid pEXJ-hSNORF1-f (ATCC Accession No. 203898).

4. A recombinant nucleic acid comprising a nucleic acid encoding a rat SNORF1 receptor, wherein the nucleic acid has a sequence identical to the sequence of the rat SNORF1 receptor-encoding nucleic acid contained in plasmid pcDNA3.1-rSNORF1-f (ATCC Accession No. 203897).

* * * * *

SEQUENCE LISTING

<160> NUMBER OF SEQ ID NOS: 4

<210> SEQ ID NO 1
<211> LENGTH: 1201
<212> TYPE: DNA
<213> ORGANISM: Homo sapiens

<400> SEQUENCE: 1

```
ctcctagaag actttgaaat tgcttccttt taaaaaaatt tttgaaagca ggaatttgag     60
aactttaaaa tagttcaaac aagaaagcaa tggtgaataa ttctcccaa gctgaggctg     120
tggagctgtg ttacaagaac gtgaacgaat cctgcattaa aactccttac tcgccaggtc    180
ctcgatctat cctctacgcc gtccttggtt ttggggctgt gctggcagcg tttggaaact    240
tactggtcat gattgctatc cttcacttca acaactgca cacacctaca aactttctga     300
ttgcgtcgct ggcctgtgct gacttcttgg tgggagtcac tgtgatgccc ttcagcacag    360
tgaggtctgt ggagagctgt tggtactttg gggacagtta ctgtaaattc catacatgtt    420
ttgacacatc cttctgtttt gcttctttat ttcatttatg ctgtatctct gttgatagat    480
acattgctgt tactgatcct ctgacctatc caaccaagtt tactgtgtca gtttcaggga    540
tatgcattgt tctttcctgg ttcttttctg tcacatacag cttttcgatc ttttacacgg    600
gagccaacga agaaggaatt gaggaattag tagttgctct aacctgtgta ggaggctgcc    660
aggctccact gaatcaaaac tgggtcctac tttgtttttct tctattcttt atacccaatg   720
tcgccatggt gtttatatac agtaagatat ttttggtggc caagcatcag gctaggaaga    780
tagaaagtac agccagccaa gctcagtcct cctcagagag ttacaaggaa agagtagcaa    840
aaagagagag aaaggctgcc aaaaccttgg gaattgctat ggcagcattt cttgtctctt    900
ggctaccata cctcgttgat gcagtgattg atgcttatat gaattttata actcctcctt    960
atgtttatga gattttagtt tggtgtgttt attataattc agctatgaac cccttgattt    1020
atgctttctt ttaccaatgg tttgggaagg caataaaact tattgtaagc ggcaaggtct    1080
taaggactga ttcgtcaaca actaatttat tttctgaaga agtagagaca gattaaaaac    1140
attactgtag agacctcaaa actaacttga aattaaggtc aagtgcaaaa ataaacactt    1200
g                                                                    1201
```

<210> SEQ ID NO 2
<211> LENGTH: 348
<212> TYPE: PRT
<213> ORGANISM: Homo sapiens

<400> SEQUENCE: 2

```
Met Val Asn Asn Phe Ser Gln Ala Glu Ala Val Glu Leu Cys Tyr Lys
  1               5                  10                  15

Asn Val Asn Glu Ser Cys Ile Lys Thr Pro Tyr Ser Pro Gly Pro Arg
             20                  25                  30

Ser Ile Leu Tyr Ala Val Leu Gly Phe Gly Ala Val Leu Ala Ala Phe
         35                  40                  45

Gly Asn Leu Leu Val Met Ile Ala Ile Leu His Phe Lys Gln Leu His
     50                  55                  60

Thr Pro Thr Asn Phe Leu Ile Ala Ser Leu Ala Cys Ala Asp Phe Leu
 65                  70                  75                  80

Val Gly Val Thr Val Met Pro Phe Ser Thr Val Arg Ser Val Glu Ser
                 85                  90                  95
```

```
Cys Trp Tyr Phe Gly Asp Ser Tyr Cys Lys Phe His Thr Cys Phe Asp
            100                 105                 110

Thr Ser Phe Cys Phe Ala Ser Leu Phe His Leu Cys Cys Ile Ser Val
        115                 120                 125

Asp Arg Tyr Ile Ala Val Thr Asp Pro Leu Thr Tyr Pro Thr Lys Phe
    130                 135                 140

Thr Val Ser Val Ser Gly Ile Cys Ile Val Leu Ser Trp Phe Phe Ser
145                 150                 155                 160

Val Thr Tyr Ser Phe Ser Ile Phe Tyr Thr Gly Ala Asn Glu Glu Gly
                165                 170                 175

Ile Glu Glu Leu Val Val Ala Leu Thr Cys Val Gly Gly Cys Gln Ala
            180                 185                 190

Pro Leu Asn Gln Asn Trp Val Leu Leu Cys Phe Leu Leu Phe Phe Ile
        195                 200                 205

Pro Asn Val Ala Met Val Phe Ile Tyr Ser Lys Ile Phe Leu Val Ala
    210                 215                 220

Lys His Gln Ala Arg Lys Ile Glu Ser Thr Ala Ser Gln Ala Gln Ser
225                 230                 235                 240

Ser Ser Glu Ser Tyr Lys Glu Arg Val Ala Lys Arg Glu Arg Lys Ala
                245                 250                 255

Ala Lys Thr Leu Gly Ile Ala Met Ala Ala Phe Leu Val Ser Trp Leu
            260                 265                 270

Pro Tyr Leu Val Asp Ala Val Ile Asp Ala Tyr Met Asn Phe Ile Thr
        275                 280                 285

Pro Pro Tyr Val Tyr Glu Ile Leu Val Trp Cys Val Tyr Tyr Asn Ser
    290                 295                 300

Ala Met Asn Pro Leu Ile Tyr Ala Phe Phe Tyr Gln Trp Phe Gly Lys
305                 310                 315                 320

Ala Ile Lys Leu Ile Val Ser Gly Lys Val Leu Arg Thr Asp Ser Ser
                325                 330                 335

Thr Thr Asn Leu Phe Ser Glu Val Glu Thr Asp
            340                 345

<210> SEQ ID NO 3
<211> LENGTH: 1061
<212> TYPE: DNA
<213> ORGANISM: Rattus norvegicus

<400> SEQUENCE: 3
cggaagactc catggagctc tgctacgaga acgtgaatgg atcttgcatt aaaagctcct      60
actcgccctg gcctcgagcc atcctctatg cggtccttgg tttgggagcc ctgctggcag     120
tgtttgggaa cttactggtc atcaccgcta tcctccactt taaacagttg cacacgccta     180
caaactttct ggtggcctcg ctggcctgtg ctgacttctt ggtgggggtg actgtgatgc     240
cctttagcac ggtgcggtct gtggagggct gctggtactt ggggacact tactgtaagt     300 tccacacgtg tttcgacacc tccttctgct tgcgtctct gtttcactta tgctgcatct     360
ccattgacag gtacgttgca gtcaccgacc cactgaccta tccgaccaag ttcaccattt     420
cggtttctgg cgtgtgcatc gctctctcgt ggttcttttc tgtcacctac agcttttcca     480
tcttttacac aggagccaac gaggaaggga ttgaggaact agtggttgct ctgacctgtg     540
tgggaggctg ccaggctcca ctgaatcaga attgggtttt actttgtttc cttttgttct     600
ttctgcccac tgtcgtcatg gtgtttctct atggtcggat attttggtg gcgaagcaac     660
```

-continued

```
aggctaggaa gatagagggt tcggccaacc aaccccaggc ctcctctgag agctacaagg    720
aaagagtagc cagacgagag aggaaggcgg ccaaaacctt ggggatcgcc atggctgcat    780
ttctcgtgtc ctggctgcca tacattatcg atgccgtgat tgatgcctac atgaacttca    840
taactcctgc ctacgtctat gagatattag tgtggtgtgt ttactataat tcagctatga    900
accctttgat atatgccttc ttttatcctt ggtttcgcaa ggcaataaaa cttattgtga    960
gtggcaaagt cttcagggct gactcatcaa gaactaatct gttctctgaa gaagcaggtg    1020
caggttaaga caatcacggc ggagagttga catccggcta g    1061
```

<210> SEQ ID NO 4
<211> LENGTH: 338
<212> TYPE: PRT
<213> ORGANISM: Rattus norvegicus

<400> SEQUENCE: 4

```
Met Glu Leu Cys Tyr Glu Asn Val Asn Gly Ser Cys Ile Lys Ser Ser
  1               5                  10                  15

Tyr Ser Pro Trp Pro Arg Ala Ile Leu Tyr Ala Val Leu Gly Leu Gly
             20                  25                  30

Ala Leu Leu Ala Val Phe Gly Asn Leu Leu Val Ile Thr Ala Ile Leu
         35                  40                  45

His Phe Lys Gln Leu His Thr Pro Thr Asn Phe Leu Val Ala Ser Leu
     50                  55                  60

Ala Cys Ala Asp Phe Leu Val Gly Val Thr Val Met Pro Phe Ser Thr
 65                  70                  75                  80

Val Arg Ser Val Glu Gly Cys Trp Tyr Phe Gly Asp Thr Tyr Cys Lys
                 85                  90                  95

Phe His Thr Cys Phe Asp Thr Ser Phe Cys Phe Ala Ser Leu Phe His
            100                 105                 110

Leu Cys Cys Ile Ser Ile Asp Arg Tyr Val Ala Val Thr Asp Pro Leu
        115                 120                 125

Thr Tyr Pro Thr Lys Phe Thr Ile Ser Val Ser Gly Val Cys Ile Ala
    130                 135                 140

Leu Ser Trp Phe Phe Ser Val Thr Tyr Ser Phe Ser Ile Phe Tyr Thr
145                 150                 155                 160

Gly Ala Asn Glu Glu Gly Ile Glu Glu Leu Val Val Ala Leu Thr Cys
                165                 170                 175

Val Gly Gly Cys Gln Ala Pro Leu Asn Gln Asn Trp Val Leu Leu Cys
            180                 185                 190

Phe Leu Leu Phe Phe Leu Pro Thr Val Val Met Val Phe Leu Tyr Gly
        195                 200                 205

Arg Ile Phe Leu Val Ala Lys Gln Gln Ala Arg Lys Ile Glu Gly Ser
    210                 215                 220

Ala Asn Gln Pro Gln Ala Ser Ser Glu Ser Tyr Lys Glu Arg Val Ala
225                 230                 235                 240

Arg Arg Glu Arg Lys Ala Ala Lys Thr Leu Gly Ile Ala Met Ala Ala
                245                 250                 255

Phe Leu Val Ser Trp Leu Pro Tyr Ile Ile Asp Ala Val Ile Asp Ala
            260                 265                 270

Tyr Met Asn Phe Ile Thr Pro Ala Tyr Val Tyr Glu Ile Leu Val Trp
        275                 280                 285

Cys Val Tyr Tyr Asn Ser Ala Met Asn Pro Leu Ile Tyr Ala Phe Phe
    290                 295                 300
```

-continued

```
Tyr Pro Trp Phe Arg Lys Ala Ile Lys Leu Ile Val Ser Gly Lys Val
305                 310                 315                 320

Phe Arg Ala Asp Ser Ser Arg Thr Asn Leu Phe Ser Glu Glu Ala Gly
                325                 330                 335

Ala Gly
```